(12) United States Patent
Caillouette

(10) Patent No.: US 6,390,991 B1
(45) Date of Patent: *May 21, 2002

(54) VAGINAL MOISTURE TEST APPARATUS AND METHOD

(76) Inventor: James C. Caillouette, 685 Oak Knoll Cir., Pasadena, CA (US) 91106

(*) Notice: Subject to any disclaimer, the term of this patent is extended or adjusted under 35 U.S.C. 154(b) by 0 days.

This patent is subject to a terminal disclaimer.

(21) Appl. No.: 09/722,212

(22) Filed: Nov. 27, 2000

Related U.S. Application Data

(63) Continuation-in-part of application No. 09/499,296, filed on Feb. 7, 2000, which is a continuation-in-part of application No. 09/118,502, filed on Jul. 17, 1998, now Pat. No. 6,117,090, which is a continuation-in-part of application No. 08/789,835, filed on Jan. 31, 1997, now Pat. No. 5,782,801, and a continuation-in-part of application No. 08/789,484, filed on Jan. 27, 1997, now Pat. No. 5,827,200, application No. 09/722,212, which is a continuation-in-part of application No. 09/072,257, filed on May 4, 1998, now Pat. No. 6,013,036, which is a continuation-in-part of application No. 08/890,748, filed on Jul. 11, 1997, now Pat. No. 5,916,176, which is a continuation-in-part of application No. 08/699,251, filed on Aug. 19, 1996, now Pat. No. 5,735,801, which is a continuation-in-part of application No. 08/570,534, filed on Dec. 11, 1995, now Pat. No. 5,762,614, which is a continuation-in-part of application No. 08/537,379, filed on Oct. 27, 1995, now Pat. No. 5,577,512, which is a continuation-in-part of application No. 08/376,830, filed on Jan. 23, 1995, now Pat. No. 5,664,579, which is a continuation-in-part of application No. 08/295,399, filed on Aug. 25, 1994, now Pat. No. 5,425,377.

(51) Int. Cl.[7] .................................. A61B 5/00
(52) U.S. Cl. ........................................ 600/584
(58) Field of Search ................ 600/570–573; 604/1; 206/569–571

(56) References Cited

U.S. PATENT DOCUMENTS

| | | |
|---|---|---|
| 2,664,879 A | 1/1954 | Hardy |
| 2,945,491 A | 7/1960 | Gibbs |
| 3,013,656 A | 12/1961 | Murphy, Jr. |
| 3,037,496 A | 6/1962 | Melges |
| 3,117,569 A | 1/1964 | Wegner |
| 3,319,621 A | 5/1967 | Schwerin |
| 3,450,129 A | 6/1969 | Avery et al. |
| 3,507,269 A | 4/1970 | Berry |
| 3,509,872 A | 5/1970 | Truhan |
| 3,777,743 A | 12/1973 | Binard et al. |
| 3,792,699 A | 2/1974 | Tobin et al. |
| 4,010,738 A | 3/1977 | Preti e tal. |
| 4,409,182 A | 10/1983 | Macklem |

(List continued on next page.)

FOREIGN PATENT DOCUMENTS

| WO | WO-A-97/46878 | 12/1997 |
|---|---|---|

OTHER PUBLICATIONS

Ronald M. Meltzer, "Vulvoganinitis", vol. 1 Chapter 37, 1994.

Ulla Molander, "Urinary Incontinence and Related Urogenital Symptoms in Elderly Women", Scandinavian Association of Obstetricians and Gynecologists, Supplement 158, vol. 72, 1993.

James P. Semmens, MD, Gorm Wagner, MD, "Estrogen Deprivation and Vaginal Function in Postmenopausal Women", 1982.

(List continued on next page.)

*Primary Examiner*—Max Hindenburg
(74) *Attorney, Agent, or Firm*—William W. Haefliger

(57) ABSTRACT

A method for detecting pH of vaginal or urethral moisture, the steps that include providing an elongated carrier; providing a pH detector on the carrier; providing a moisture receiver in association with the carrier, and via which a sample of vaginal or urethral moisture is applicable to a detector to effect a changed color thereof; and providing a pH correlating color comparison means in sufficiently close association with the detector to allow visual comparison of the changed color exhibited by the detector with a pH correlated color provided by measurement means.

18 Claims, 1 Drawing Sheet

U.S. PATENT DOCUMENTS

| | | | |
|---|---|---|---|
| 4,457,313 | A | 7/1984 | Alter |
| 4,784,158 | A | 11/1988 | Okimoto |
| 4,788,985 | A | 12/1988 | Manning et al. |
| 4,820,259 | A | 4/1989 | Stevens |
| 4,862,899 | A | 9/1989 | Bucaro |
| 5,063,930 | A | 11/1991 | Nucci |
| 5,147,288 | A | 9/1992 | Schiavo |
| 5,425,377 | A | 6/1995 | Caillouette |
| 5,577,512 | A | 11/1996 | Caillouette |
| 5,660,790 | A | 8/1997 | Lawrence et al. |
| 5,664,579 | A | 9/1997 | Caillouette |
| 5,735,801 | A | 4/1998 | Caillouette |
| 5,738,634 | A | 4/1998 | Caillouette |
| 5,762,614 | A | 6/1998 | Caillouette |
| 5,782,801 | A | 7/1998 | Caillouette |
| 5,827,200 | A | 10/1998 | Caillouette |
| 5,916,176 | A | 6/1999 | Caillouette |
| 6,013,036 | A | 1/2000 | Caillouette |
| 6,117,090 | A | 9/2000 | Caillouette |

OTHER PUBLICATIONS

Gloria Bachmann, "The Estradio Vaginal Ring—A Study of Existing Clinical Data", Maturitas 22 Suppl. (1995) S21–S29, 1995.

Peter Smith, "Estrogens and the Urogenital Tract", Dept. of Obstetrics & Gynecology, University Hospital, S–751 85 Uppsala, Sweden, 1993.

Richard Amsel, MD. et al.,"Nonspecific Vaginitis—Diagnostic Criterial and Microbial and Epidemiologic Associations", The American Journal of Medicine, vol. 74, Jan., 1983.

Kirk C.S. Chen et al, "Biochemical Diagnosis of Vaginitis: Determination of Diamines in Vaginal Fluid", The Journal of Infectious Diseases, vol. 145, No. 3, Mar. 1982.

Kirk C.S. Chen et al, "Amine Content of Vaginal Fluid From Untreated and Treated Patients With Nonspecific Vaginitis", The American Society for Clinical Investigations, Inc., vol. 63, May, 1979, pp. 828–835.

Culley C. Carson, MD, et al, "Current Management of UTI in Women", Contemporary OB/GYN, Fall, 2000, p. 3, p. 17.

James C. Caillouette, MD, et al., "Vaginal pH as a Marker for Bacterial Pathogens and Menopausal Status", American Journal of Obstetrics and Gynecology, 1996, vol. 176, No. 6, pp. 1270–1277.

Montserrat Garcia–Closas, MD, et al., "Epidemiologic Determinants of Vaginal pH", American Journal of Obstetrics and Gynecology, 1998, vol. 180, No. 5, pp. 1060–1066.

VAGINAL MOISTURE TEST APPARATUS AND METHOD

This application is a continuation-in-part of prior U.S. application Ser. No. 09/499,296 filed Feb. 7, 2000, which is a continuation-in-part of prior U.S. application Ser. No. 09/118,502 filed Jul. 17, 1998, now U.S. Pat. No. 6,117,090, which is a continuation-in-part of prior U.S. application Ser. No. 08/789,484 filed Jan. 27, 1997, now U.S. Pat. No. 5,827,200, and a continuation-in-part of prior U.S. application Ser. No. 08/789,835 filed Jan. 31, 1997, now U.S. Pat. No. 5,782,801, and this application is also a continuation-in-part of prior U.S. application Ser. No. 09/072,257 filed May 4, 1998, now U.S. Pat. No. 6,013,036, which is a continuation-in-part of prior U.S. application Ser. No. 08/890,748 filed Jul. 11, 1997, now U.S. Pat. No. 5,916,176, which is a continuation-in-part of prior U.S. application Ser. No. 08/699,251 filed Aug. 19, 1996, now U.S. Pat. No. 5,735,801, which is a continuation-in-part of prior U.S. application Ser. No. 08/570,534 filed Dec. 11, 1995, now U.S. Pat. No. 5,762,614, which is a continuation-in-part of prior U.S. application Ser. No. 08/537,379 filed Oct. 27, 1995, now U.S. Pat. No. 5,577,512, which is a continuation-in-part of prior U.S. application Ser. No. 08/376,830 filed Jan. 23, 1995, now U.S. Pat. No. 5,664,579, which is a continuation-in-part of prior U.S. application Ser. No. 08/295,399 filed Aug. 25, 1994, now U.S. Pat. No. 5,425,377.

BACKGROUND OF THE INVENTION

This invention relates generally to testing of body fluid, one example being pH measurement of body fluid, such as vaginal and/or urethral fluid, or moisture, and more particularly, to a rapid, easily performed method of such testing, or obtaining such measurement.

There is continued need to obtain pH measurement of vaginal fluid, as for example in the determination of whether amniotic fluid has escaped into the vagina, during late pregnancy. Amniotic fluid is normally alkaline, whereas vaginal moisture is normally acidic. This difference enables testing for pH, using a test strip, such as a Nitrazine® strip, typically handled by forceps when inserted into the vagina, urethra or other body openings for pH test purposes; however, the procedure and subsequent procedures to determine acidity or alkalinity requires considerable manipulation, including cutting of a test strip, grasping of the cut strip by forceps manipulation, subsequent insertion with risk of separation of the strip from the forceps, recovery of the strip, and its examination. There is also need to obtain pH measurement of urethral moisture; to test for need for estrogen treatment, and to test for presence of pathogenic bacteria.

Further, there is need for a simple, rapidly carried out method which obviates problems associated with conventional procedure, one example being need to assuredly test vaginal moisture within the vagina, but spaced from the cervix, and also to test urethral moisture.

SUMMARY OF THE INVENTION

It is a major object of the invention to provide a significantly improved vaginal probe apparatus which meets the above need, and overcomes prior problems, as referred to. Basically, the apparatus includes:

a) an elongated carrier, b) a pH detector on the carrier, c) a moisture receiver in association with the carrier, and via which a sample of vaginal or urethral moisture is applicable to said detector to effect a changed color thereof, d) a pH correlating color comparison means in sufficiently close association with the detector to allow visual comparison of the changed color exhibited by the detector with a pH correlated color provided by the measurement means.

Another object is to provide a moisture receiver carried in association with the carrier in the form of a card, and via which a sample of vaginal or urethral moisture is applicable to the detector, to effect a changed color thereof. As will appear, the moisture receiver is advantageously carried by the card for ease of removal and use, as by insertion into the vagina to obtain the moisture sample. The receiver may comprise a swab carried by a handle to provide a probe which is removably attached to the card. The handle, as for example a stick, is typically removably attached to the card at a side thereof which is the same as the card side at which the detector and color comparison elements are presented.

A further object is to provide color comparison elements located on an elongated strip elongated in a direction, which is generally the same as the detector length direction.

Yet another object is to provide a method for detecting pH of vaginal or urethral moisture, and including the steps:

a) providing an elongated carrier, b) providing a pH detector such as a detector strip on the carrier, c) providing a moisture receiver in association with the carrier, and via which a sample of vaginal or urethral moisture is applicable to said detector to effect a changed color thereof, d) and providing a pH correlating color comparison means in sufficiently close association with the detector or detector strip to allow visual comparison of the changed color exhibited by said detector with a pH correlated color provided by that measurement means.

As referred to, the carrier may be provided in the form of a card; the detector may be provided in the form of an elongated strip on the card; and the handle may be removably attached to the card at a side thereof the same as the card side at which the detector and color comparison elements are presented.

The three components including the handle, detector and color comparison elements may all be presented at the same side of the card for ease and readiness of use, and they may all extend in generally parallel relation to facilitate such ready usage, as by holding the card with one hand, and swiping the swab along the surface of the detector, with the user's other hand holding the handle, whereby there is no need for manual touching of the detector.

A further object is to provide the detector as a means for detection of a vaginal or urethral moisture factor, as for example one of the following:

i) a pH indicator ii) an amine pressure indicator iii) a bacteria pressure indicator, for purposes as will appear.

These and other objects and advantages of the invention, as well as the details of an illustrative embodiment, will be more fully understood from the following specification and drawings, in which:

DRAWING DESCRIPTION

DETAILED DESCRIPTION

Figure 1:
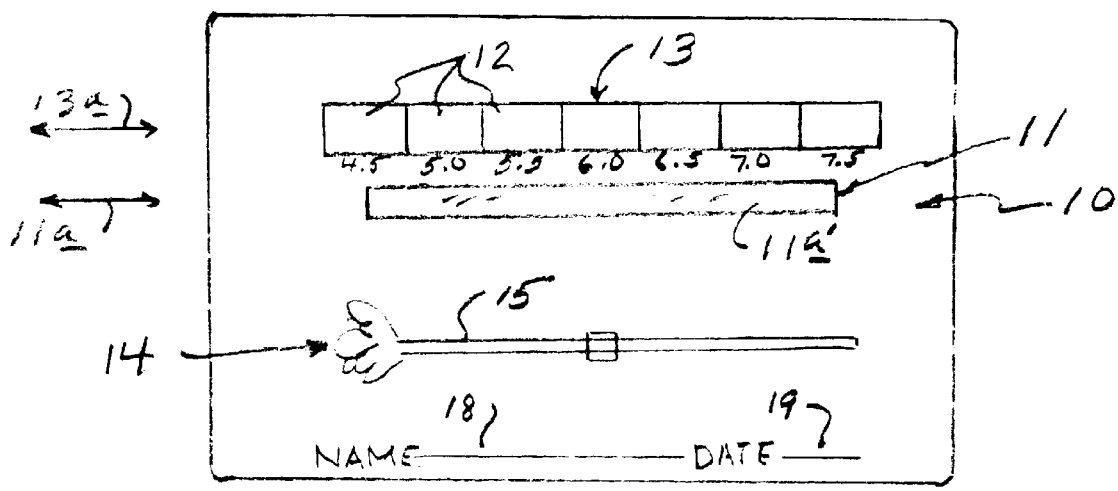
FIG. 1 is a frontal view of a package including a carrier card, with color comparison elements, detector, and moisture receiver handle carried by the card.
Figure 2:
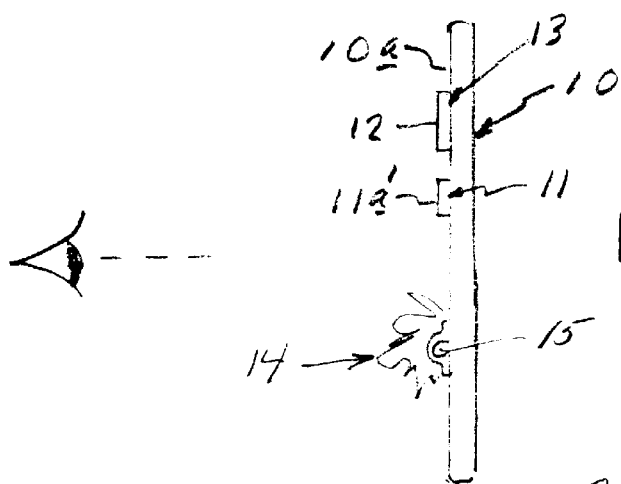
FIG. 2 is an edge view taken on lines 2—2 of FIG. 1.

Referring to FIGS. 1 and 2, they show:

a) a carrier, in the form of a card 10, b) a detector in the form of an indicator strip 11 on the card, and extending in a first elongation direction 11a, c) color comparison measurement elements 12, for example on a strip 13, carried by the card to extend in series in a second elongation direction 13a, in such proximity to the detector 11 as to allow their color comparisons with the color of the detector 11, after exposure of the detector to vaginal or urethral moisture, a factor (such as pH) of which is to be determined.

The strips 11 and 13 may be adhered, as by bonding, to the card surface 10a, facing the viewer or user as seen in FIG. 2. Directions 11a and 13a are generally the same, and may be parallel.

Also shown is a moisture receiver, as for example a swab 14, carried in association with the card, and via which a sample of vaginal or urethral moisture is applicable to the detector, to effect a changed color thereof. The moisture receiver is typically carried by or on a handle 15, and so that the receiver is removably carried by the card. The handle may take the form of a stick removably attached to the card face 10a, as by a short strip of adhesive tape 16. Receiver 14 and handle 15 may be regarded as a probe. Accordingly, all the components 11, 13 and 14 are presented at the same side (front) of the card, for ready use in testing for the vaginal or urethral moisture factor. During such testing, the card edges 10a and 10b, for example, may be grasped by the fingers of one hand of the user, or tester, and the handle 15 may be grasped by fingers of the other hand of the user, to swipe the moistened swab 14 on and along the exposed surface 11a of the detector, lengthwise thereof, whereby the user's fingers never touch the swab or the detector.

Handle 15, as carried, may extend parallel to directions 11a and 13a, as shown, enhancing readiness and rapidity of test use. User's or tester's name and test date indicia are shown at 18 and 19, and may be presented on the card for recording.

The detector 11 typically comprises an indicator element or strip, as for example one of the following:

i) a pH indicator ii) an amine indicator iii) a bacteria indicator.

A typical pH indicator or detector typically takes the form of a Nitrazine® strip adhered to the side 10a of the card, as for example by double sided adhesive tape. After exposure of the strip to vaginal moisture, its changed color (according to pH level) is compared with the series of color comparison elements 12 in the form of bands. Each band has a different color corresponding to a pH level color to which the detector strip may change. See for example the indicated pH levels 4.5, 5.0, 5.5, 6.0, 6.5, 7.0 and 7.5 adjacent the color bands. The bands may be provided on a strip 13 adhered to the surface 10a of the card. Paper strips providing such elements are known, and sold under the name HYDRION papers, by Micro Essential Laboratory Inc., Brooklyn, N.Y. 11210. The band for pH 4.5 is typically bright yellow; the band for pH 6.0 is olive in color; and the band for pH 7.5 is navy blue.

In use, vaginal or urethral moisture is applied to the surface of strip 11 to produce a color change as referred to above. This enables ready visual comparison of the color of the detector strip 11 with the closest color of one of the bands, enabling a pH determination. Detector strip 11 extends lengthwise, in proximity to all or most of the bands 13.

Figure 3:
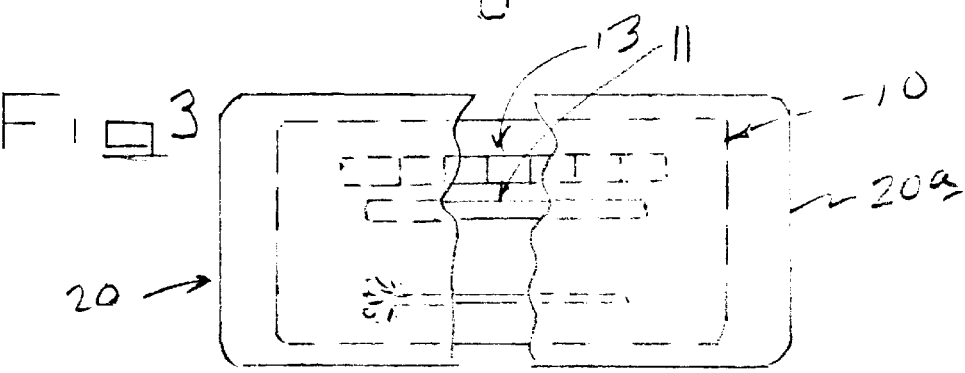
FIG. 3 is a frontal view of the FIG. 1 package inserted into a protective envelope, for removal at time of use.

The package as seen in FIGS. 1 and 2 may be conveniently stored prior to use in a protective receptacle 20, as seen in FIG. 3, prior to use. At time of use, the right end 20a of the receptacle is opened, and the card 10 is withdrawn, for use in gathering vaginal moisture as described. After such color comparison use, the card and probe may be inserted back into the receptacle 20, for ease of disposal, or storage, or subsequent review.

The color changing reactant may be applied to or incorporated on, or in the interstices of the receiver, and may for example, be one or more of the following: Bromocresol Green, Bromocresol Purple, Nitrazine Yellow, Bromophenol Blue, and equivalents.

An alternative confirmation step of obtaining a visual comparison of the color changed zone on the receiver or swab 14 with a color, or different colors, or band color shades, on 13, enables a test wherein one color band may indicate presence of putrecine on the swab; another color band may indicate presence of cadaverine; and a third band may have another color or color shade close to but different from the first two, and so indicating absence of putrecine or cadaverine, i.e. facilitating an amine test when compared side-by-side with the color on the receiver 14. Such amine detection indicates presence of pathogenic bacteria in the moisture from the vagina or urethra.

Typically, the thicknesses of strips 11 and 13 are less than card thickness.

The test apparatus including the card as disclosed herein may be regarded as a test kit, which can be easily filed or stored after use.

I claim:

1. In the method for detecting pH of vaginal or urethral moisture, the steps that include a) providing an elongated carrier, b) providing a pH detector on the carrier, c) providing a moisture receiver in association with the carrier, and via which a sample of vaginal or urethral moisture is applicable to said detector to effect a changed color thereof, d) and providing a pH correlating color comparison means in sufficiently close association with said detector to allow visual comparison of the changed color exhibited by said detector with a pH correlated color provided by said measurement means.

2. The method of claim 1 wherein said detector is provided in the form of an elongated strip and said color comparison means is provided in the form of a strip of material that is elongated in a direction related to the elongated direction of said detector strip to facilitate said color comparison.

3. The method of claim 1 wherein said carrier is provided in the form of a card.

4. The method of claim 3 including adhering said color comparison measurement strip to said card to have thickness that is everywhere less than the thickness of said card adjacent the measurement strip.

5. The method of claim 2 wherein said color comparison measurement strip exhibits a series of comparison colors spaced apart linearly, and including locating said color comparison measurement strip in such relation to the detector strip as to position said linearly spaced series of colors substantially in parallel relation with said elongated detector strip.

6. The method of claim 1 including mounting said receiver onto said carrier to be releasable therefrom for use in obtaining said sample.

7. The method of claim 6 including providing a handle carrying said receiver and via which said releasable mounting is achieved.

8. The method of claim 7 wherein said receiver is a swab.

9. In combination:
   a) a support, in the form of a card,
   b) a pH detector on the card, the detector having a first elongation direction,
   c) color comparison elements carried by the card to extend in a second elongation direction to allow their color comparison with said pH detector after exposure of said detector to vaginal or urethral moisture the pH of which is to be determined.

10. The combination of claim 9 including a moisture receiver carried in association with the card, and via which a sample of vaginal or urethral moisture is applicable to the detector, to effect a changed color thereof.

11. The combination of claim 10 wherein the receiver is removably carried by the card.

12. The combination of claim 9 wherein said color comparison elements are located on a strip elongated in a direction generally the same as said first direction.

13. The combination of claim 11 including a handle carrying the receiver, the handle removably attached to the card at a side thereof the same as the card side at which the detector and color comparison elements are presented.

14. The combination of claim 13 wherein said handle comprises a stick.

15. The combination of claim 13 wherein the handle, detector, and color comparison elements on a strip are all carried at the same side of the card.

16. The combination of claim 13 wherein the handle, detector and comparison elements all extend in generally parallel relation on the card.

17. In the method for detecting vaginal or urethral moisture factor of vaginal or urethral moisture, the steps that include
   a) providing an elongated carrier,
   b) providing a vaginal or urethral moisture factor detector on the carrier,
   c) providing a moisture receiver in association with the carrier, and via which a sample of vaginal or urethral moisture is applicable to said detector to effect a changed color thereof,
   d) and providing a vaginal or urethral moisture factor correlating color comparison means in sufficiently close association with said detector to allow visual comparison of the changed color exhibited by said detector with a vaginal or urethral moisture factor correlated color provided by said measurement means.

18. The method of claim 1 wherein said moisture factor detector is one of the following:
   i) a pH indicator,
   ii) an amine indicator,
   iii) a bacteria indicator.

* * * * *